United States Patent [19]

Mayer et al.

[11] 4,312,996
[45] Jan. 26, 1982

[54] BENZODIAZEPINE INTERMEDIATES

[75] Inventors: Joseph Mayer, New York, N.Y.; Lydia Peer; Esther Babad, both of West Orange, N.J.

[73] Assignee: Schering Corporation, Kenilworth, N.J.

[21] Appl. No.: 221,136

[22] Filed: Dec. 29, 1980

[51] Int. Cl.³ .................. C07C 143/822; C07C 97/10; C09B 11/02
[52] U.S. Cl. ........................................ 564/92; 564/328
[58] Field of Search ........................................... 564/92

[56] References Cited

U.S. PATENT DOCUMENTS 2,353,262  7/1944  Peterson et al. ................. 564/92 X
3,846,477  11/1974  Welstead et al. ................. 564/92 X Primary Examiner—John Doll
Attorney, Agent, or Firm—Paul H. Ginsburg

[57] ABSTRACT

A compound of the formula

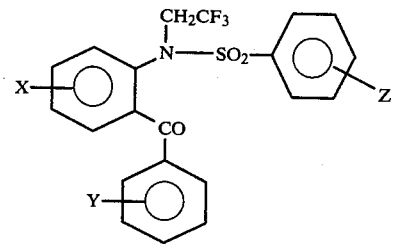

wherein X and Y are independently selected from hydrogen, halogen, trifluoromethyl, nitro, $C_1$ to $C_6$ alkyl and $C_1$ to $C_6$ alkoxy, and Z is $C_1$ to $C_6$ alkyl or hydrogen is disclosed.

4 Claims, No Drawings

BENZODIAZEPINE INTERMEDIATES

The present invention relates to novel intermediates that are useful in the preparation of 1,4-benzodiazepines, which are well known therapeutic agents, and to processes for the preparation of said intermediates.

The compounds of the present invention are compounds of the formula

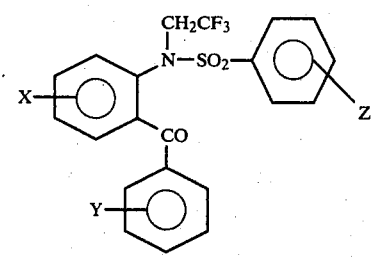

wherein X and Y are independently selected from hydrogen, halogen, trifluoromethyl, nitro, $C_1$ to $C_6$ alkyl and $C_1$ to $C_6$ alkoxy, and Z is $C_1$ to $C_6$ alkyl or hydrogen.

In the above formula, the alkyl groups or portions of such alkyl groups may be linear, branched or cyclic, and halogen includes fluorine, chlorine, bromine and iodine.

The present invention also relates to a process for the preparation of compounds of the formula

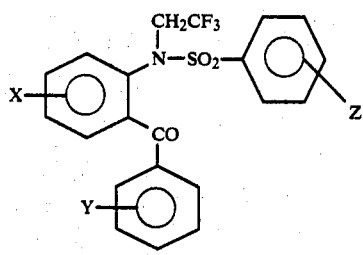

wherein X and Y are independently selected from hydrogen, halogen, trifluoromethyl, nitro, $C_1$ to $C_6$ alkyl and $C_1$ to $C_6$ alkoxy, and Z is $C_1$ to $C_6$ alkyl or hydrogen, comprising alkylating a compound of the formula

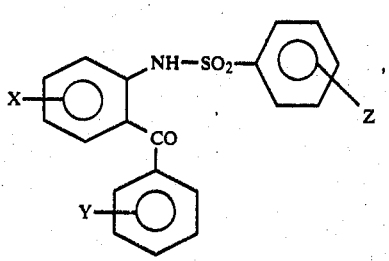

wherein X, Y and Z are as defined above, with a compound of the formula

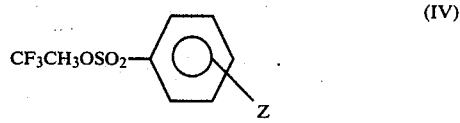

The compounds of the present invention may be hydrolyzed to prepare compounds of the formula

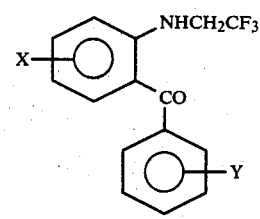

wherein X and Y are independently selected from hydrogen, halogen, trifluoromethyl, nitro, $C_1$ to $C_6$ alkyl and $C_1$ to $C_6$ alkoxy, which are key intermediates in the preparation of benzodiazepines such as halazepam. In fact, preparation of the compound of the formula (X), wherein X is chloro and Y is hydrogen, by the methods referred to above is preferred because it avoids the use of expensive or hazardous substances such as trifluoroethyliodide or perchloromethylmercaptan.

The following reaction scheme illustrates the processes of the present invention:

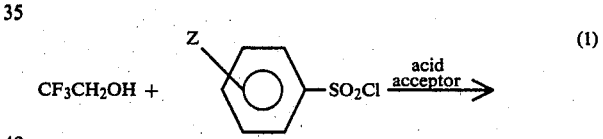

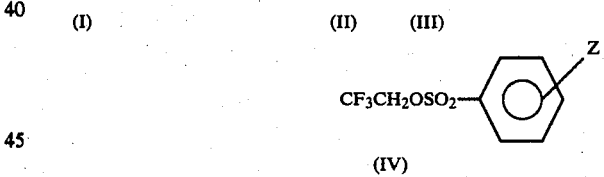

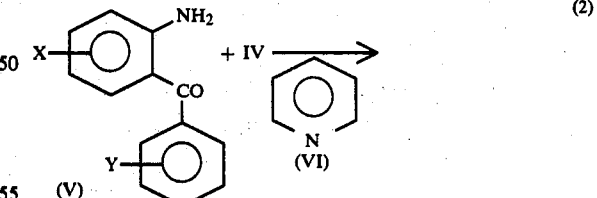

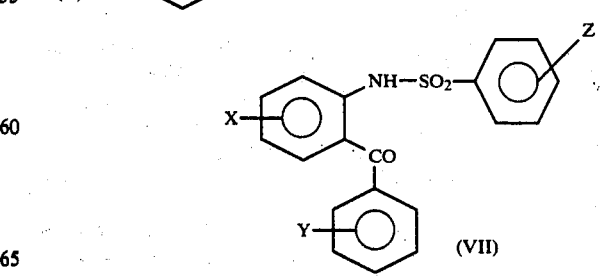

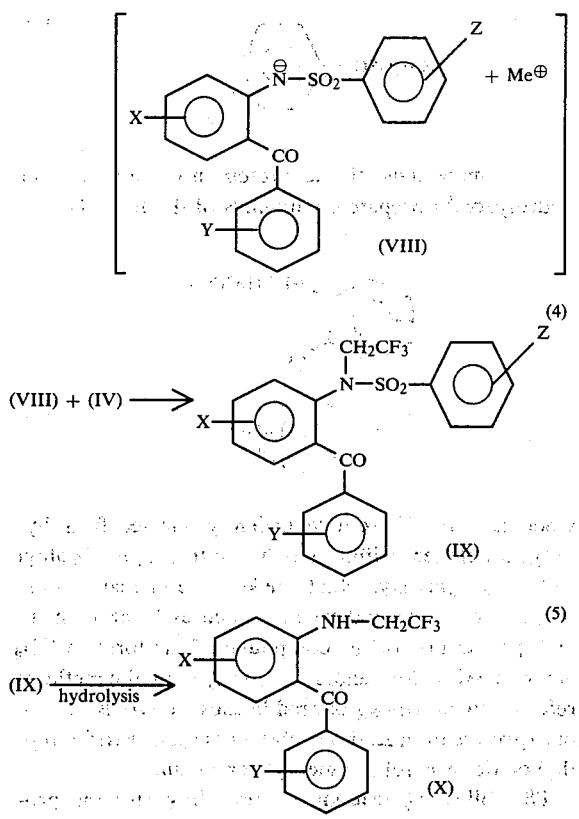

Examples of the acid acceptors that may be used in the process of the present invention are triethylamine and pyridine.

The solvent used in steps 1 to 4 should be an inert solvent, preferably a high boiling inert solvent having a boiling point of about 170° to 210° C. Examples of such solvents are tetralin or commercially available mixed aromatic solvents.

An example of a base that may be used in step 3 is a mixture of sodium methylate and potassium methylate, in a weight:weight ratio of about 1:1. Preferably, the base is a mixture of $Na_2CO_3$ and $K_2CO_3$ in a weight:weight ratio of about 1:1.

The hydrolysis of step 5 is preferably performed in an acid medium. For example, in a mixture of toluene and concentrated sulfuric acid.

EXAMPLE

(A) 2,2,2-Trifluoroethyl Benzensulfonate

Into a two liter, three necked flask equipped with stirrer, thermometer and addition funnel charge 150 g of trifluoroethanol, 360 ml of dichloromethane and 303 g of benzenesulfonyl chloride (Aldrich, 96%). Add dropwise to the stirred solution 212 g of triethyl amine at 20°-25° C. Cooling is necessary during the addition. When about a third of the triethyl amine has been added, a white precipitate starts to form. After the addition is complete, continue to stir the reaction mixture for 2 hours at room temperature.

Add 185 ml of water and stir for approximately 4 hours until the excess benzenesulfonyl chloride has been completely hydroyzed. This is determined by spotting a drop of the organic layer on a silica gel plate. Develop with $Cl_2CH_2$:hexane=2:1, in two runs, one of 4 cm and the second of 8 cm. No benzenesulfonyl chloride should be visible under ultraviolet light. If sulfonyl chloride is still present, continue to stir for another hour, or for as long as necessary to complete the hydrolysis. Separate and wash the organic bottom layer with 225 ml of water (the pH of the wash is about 10); 600 ml of ice cold aqueous 5% $H_2SO_4$ (careful exothermic!) (the pH of the wash should be less than 1); 225 ml of water; 225 ml of aqueous 2% $NaCHO_3$ (the pH of the wash should be about 8) and finally with 225 ml of water (the pH of the wash should be 6.5 to 7).

Dry the organic layer over $Na_2SO_4$, simultaneously treating with 7.2 g of Darco (G60) decolorizing carbon. Filter through a Celite bed and wash the cake with 25 ml of methylene dichloride. Remove the solvent on a rotary evaporator under reduced pressure (100-120 mm/Hg) at 60° C. to obtain 390 g of a light yellow oil (108.2% of theory).

This material is used as such in the alkylation step (C) described below.

(B) 2-Benzenesulfonamido-5-chlorobenzophenone (in solution)

Into a one liter three necked flask equipped with stirrer, thermometer and addition funnel charge: 74.2 g of 2-amino-5-chloro-benzophenone, 148.4 ml of diethylbenzene (Aldrich, mixture of o-, m- and p-isomers b.p. 180°-182° C.) and 64.8 g of benzenesulfonyl chloride (Aldrich, 96%).

Over a 30 minute period, add dropwise to the stirred suspension at 20°-25° C., 35.3 g of pyridine. The addition is slightly exothermic; intermittent cooling is required. Continue to stir for 18 to 20 hours at room temperature and then check for completion of the reaction. The content of unreacted 2-amino-5-chloro-benzophenone should be below 0.5%. This is determined by spotting a drop of the organic solution on a silica gel plate against a solution of 50 mg of 2-amino-5-chlorobenzophenone in 20 ml of methylene dichloride (this concentration corresponds to 0.5%). Develop with $Cl_2CH_2$ in an $NH_3$ atmosphere (the filter paper lining of the TLC tank is wetted with 1.2 ml of concentrated aqueous $NH_4OH$) and observe under ultraviolet light. Add 20 ml of water to the reaction mixture and stir for 3 hours at room temperature. Initially some cooling is required to prevent the temperature from rising.

Check the organic layer for the absence of benzenesulfonyl chloride. This is determined by spotting a drop of the organic layer on a silica gel plate. Develop with $Cl_2CH_2$:hexane=2:1, a 6 cm run, and observe under ultraviolet light. No benzenesulfonyl chloride should be visible. If the hydrolysis of benzenesulfonyl chloride is not complete, continue to stir for another hour, or longer if necessary, until hydrolysis is complete. Once benzenesulfonyl chloride is found to be absent, separate and discard the bottom aqueous layer. Add 50 ml of diethylbenzene to the organic phase and wash with 200 ml of 2% w/v $H_2SO_4$ in 20% brine (the pH of the wash should be less than 1), and then three times with 50 ml of 20% brine, until the pH of the wash is 6.5. Finally wash with 50 ml of saturated brine and separate the layers carefully. The organic layer containing the product is used in the next step (C) without prior drying, but if desired, the product may be isolated and recrystallized from ethanol to yield a white solid having a melting point of 60°-61° C.

If desired, similarly prepare the tosyl sulfonamido-5-chlorobenzophenone, m.p. 120°–121° C., and utilize it for the alkylation step described below.

(C) 2-(N-beta,beta,beta-Trifluoroethyl)-benzenesulfonylamido-5-chlorobenzophenone Into a two liter three necked flask equipped with mechanical stirrer, a Dean-Start tube, reflux condenser, thermometer and addition funnel charge the solution of 2-benzenesulfonamido-5-chloro-benzophenone as obtained from the previous step B, 40 ml of diethylbenzene, 11 g of anhydrous sodium carbonate and 14.4 g of anhydrous potassium carbonate.

Heat the suspension gently but with vigorous stirring. At about 100° C., the consistency of the mixture changes and a new yellow precipitate is being formed. Simultaneously, conspicuous evolution of $CO_2$ takes place. At about 160° C., the water formed in the reaction of 2-benzene-sulfonamido-5-chlorobenzophenone with the carbonates starts to distill. As the water is being removed azeotropically, the temperature rises to 180°–184° C. Continue to reflux the mixture at 180°–184° C. After about 30 minutes of reflux at constant temperature, add 0.416 moles of 2,2,2-trifluoroethyl benzenesulfonate in a fast stream.

Continue to reflux for 40 hours. The temperature will gradually increase from about 185° C. to 188°–190° C. at the end of 40 hours. All along, continue to remove (by azeotropic distillation) traces of water still present or being formed during this time. At the end of the 40 hours the mixture is a gently foaming, light brown, thin suspension with some salts adhering to the walls of the flask. Cool to about 50° C. and add 200 ml of ice cold water. A thick, oily but well stirrable slurry results.

Adjust the pH to 7 with 70–80 ml of aqueous 5% $H_2SO_4$. Steam distill the diethylbenzene, using about 800 g of steam to remove the solvent. A total of about 240 ml of diethylbenzene is obtained.

During the steam distillation, the mixture turns into a granular suspension. Cool to about 80° C. and extract the product with 500 ml of toluene. Separate and reextract the waters with 100 ml of toluene. All extractions and the subsequent wash have to be carried out hot, at about 75°–80° C. Wash the combined organic layers with 300 ml of hot water and carefully separate the phases. The hot toluene solution is ready to be used in the next step, but the product may be isolated and recrystallized from methylene dichloride-hexane as a white crystalline solid, having a melting point of 175°–176° C.

Hot extractions are necessary because of the limited solubility of the title compound of this step in toluene (1 g in 3 ml of toluene at 80° C. and in 20 ml at room temperature). This title compound is also soluble in methylene dichloride (1 g in 5 ml at room temperature) but toluene as solvent was preferred.

(D) Hydrolysis to 2-(N-beta,beta,beta-Trifluoroethyl)-amino-5-chlorobenzophenone Into a two liter three necked flask equipped with stirrer, thermometer, Dean-Stark tube and reflux condenser charge the hot toluene solution of 2-(N-beta,beta,beta-trifluoroethyl)-benzenesulfonyl-amido-5-chlorobenzophenone as obtained from the previous step (C) (approximately 700–750 ml). Remove, azeotropically, all of the water through the Dean-Stark tube. Then distill off about 300 ml of toluene. Cool the mixture to room temperature, with stirring, and obtain a fine suspension of 2-(N-beta,beta,beta-trifluoroethyl)-benzenesulfonyl-amido-5-chlorobenzophenone in the toluene. From an addition funnel, add dropwise 145 ml of concentrated sulfuric acid while cooling the mixture to maintain 20°–25° C. Continue to stir at room temperature until the reaction is complete, which usually takes about 2 to 3 hours. This is determined by withdrawing a sample from the stirred mixture, diluting with a small amount of water, extracting with methylene dichloride, and spotting the organic layer on a silica gel TLC plate and developing with 2:1 $Cl_2CH_2$:hexane. After the reaction is complete, quench on 2.8 liters of water and 100–200 g of ice. Stir briefly and separate. Extract the water layer with 145 ml of toluene, filter the combined toluene layers from and insoluble particles and wash with 145 ml of aqueous 2% NaOH (the pH of the wash should be no higher than 9; if higher, repeat the wash with $NaHCO_3$) and finally with 145 ml of water once or twice until the pH of wash is not higher than 7.

Dry over $Na_2SO_4$, simultaneously treating with 5 g of Darco (G 60) decolorizing carbon. Filter through a celite bed and wash the cake twice with 25 ml of toluene. Remove the solvent to obtain 130 g. of a crude oil which crystallizes partially on standing. Dissolve the residue in 70 ml of boiling 2 B ethanol. Cool to room temperature while providing efficient stirring and continue to stir at room temperature for at least 30 minutes. Filter the paste-like mixture and wash the cake with 50 ml of ice-cold 2 B ethanol followed by 50 ml of hexane. Dry in a draft oven at 40°–50° C. to obtain 74–77 g of bright yellow crystalline material having a melting point of 97°–99° C.

What is claimed is:

1. A compound of the formula

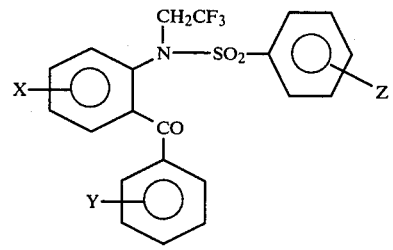

wherein X and Y are independently selected from hydrogen, halogen, trifluoromethyl, nitro, $C_1$ to $C_6$ alkyl and $C_1$ to $C_6$ alkoxy, and Z is $C_1$ to $C_6$ alkyl or hydrogen.

2. A compound according to claim 1, wherein X is halogen, Y is hydrogen and Z is methyl.

3. A compound according to claim 1, wherein X is halogen and Y and Z are hydrogen.

4. A compound according to claim 1, wherein X is chloro and Y and Z are hydrogen.

* * * * *